United States Patent [19]
Czech

[11] Patent Number: 5,981,681
[45] Date of Patent: Nov. 9, 1999

[54] SILICONE AMINOPOLYALKYLENEOXIDE BLOCK COPOLYMERS

[75] Inventor: Anna Czech, Cortlandt Manor, N.Y.

[73] Assignee: Witco Corporation, Greenwich, Conn.

[21] Appl. No.: 09/098,363

[22] Filed: Jun. 17, 1998

Related U.S. Application Data

[62] Division of application No. 08/810,408, Mar. 4, 1997, Pat. No. 5,807,956.
[60] Provisional application No. 60/012,732, Mar. 4, 1996.

[51] Int. Cl.$^6$ ..................................... C08G 77/26
[52] U.S. Cl. ............... 528/27; 528/38; 424/70.122; 556/425; 556/445; 556/423; 525/476; 8/DIG. 1; 8/127.51; 8/128.3; 8/115.64; 8/196; 428/447
[58] Field of Search ................. 528/38, 27; 428/447; 525/476; 556/425, 445, 423; 8/DIG. 1, 115.64, 128.3, 127.51, 196; 424/70.122

[56] References Cited

U.S. PATENT DOCUMENTS

| | | | |
|---|---|---|---|
| 2,843,560 | 7/1958 | Mika | 528/27 |
| 3,620,821 | 11/1971 | Johnsom | 525/476 |
| 3,655,420 | 10/1982 | Tichenor | 117/138.8 A |
| 4,101,272 | 7/1978 | Guise | 8/127.6 |
| 4,283,519 | 8/1993 | Pines et al. | 508/26 |
| 4,624,998 | 11/1986 | Keil | 525/476 |
| 4,684,709 | 8/1987 | Ona et al. | 528/15 |
| 4,757,121 | 7/1988 | Tanaka et al. | 528/27 |
| 4,786,667 | 11/1988 | Shimizu et al. | 523/435 |
| 4,833,225 | 5/1989 | Schaefer et al. | 528/28 |
| 4,910,015 | 3/1990 | Sung | 424/78 |
| 4,933,415 | 6/1990 | Shimizu et al. | 528/27 |
| 5,075,403 | 12/1992 | Kirk et al. | 528/15 |
| 5,252,233 | 10/1993 | Czech | 252/8.6 |
| 5,362,484 | 11/1994 | Wood et al. | 424/70 |
| 5,364,923 | 11/1994 | Mikami | 528/27 |
| 5,807,956 | 9/1998 | Czech | 528/28 |

Primary Examiner—Margaret G. Moore
Attorney, Agent, or Firm—Edward K. Welch, II; Andrew S. Reiskind; Timothy X. Witkowski

[57] ABSTRACT

The present invention discloses non-hydrolyzable, block, $(AB)_nA$ type, copolymers comprising alternating units of polysiloxane and amino-polyalkyleneoxide and provides a method for the preparation of these copolymers. Also provided is the use of these copolymers as softeners, in particular durable, hydrophilic textile softeners, which improve tactile properties of the textiles substrates treated with the commercial soil release finishes, without substantially detracting from their properties. The copolymers of the present invention have alternating units of polysiloxane $[X(C_aH_{2a}O)_bR^2[(SiO(R^1)_2]_cSi(R^1)_2R^2(C_aH_{2a}O)_bX]$ and polyalkyleneoxides $[YO(C_aH_{2a}O)_dY]$ wherein $R^1$ is a $C_1$ to $C_4$ alkyl, preferably methyl, $R^2$ is a divalent organic moiety, X and Y are divalent organic groups selected from a secondary or tertiary amine and a ring opened epoxide, such that when X is a ring opened epoxide, Y is an amine and vice versa, a=2 to 4, preferably 2 to 3, b=0 to 100, d=0 to 100, b+d=1 to 100, preferably 10 to 50, and c=1 to 500, preferably 10 to 100.

18 Claims, No Drawings

SILICONE AMINOPOLYALKYLENEOXIDE BLOCK COPOLYMERS

This application claims priority from U.S. Provisional Application No. 60/012,732 filed Mar. 4, 1996, and is a divisional of U.S. Ser. No. 08/810,408 filed Mar. 4, 1997, now U.S. Pat. No. 5,807,956.

BACKGROUND OF THE INVENTION

Non-hydrolyzable siloxane-polyalkyleneoxide block copolymers of the $(AB)_nA$ type, i.e., with alternating siloxane and organic, mostly polyether, blocks, are known in the prior art. Methods of preparation of such copolymers is provided in U.S. Pat. No. 4,242,466. U.S. Pat. No. 4,833,225 discloses $(AB)_nA$ type silicone polyquats derived from an epoxy endblocked polysiloxane and low molecular weight diamines with tertiary amino endgroups. The resulting copolymers therein are polyquaternary and do not contain polyalkyleneoxide units in the structure.

U.S. Pat. No. 4,101,272 provides a process for improving properties of fibrous materials, in which these materials are treated with a composition of epoxy modified polyorganosiloxanes and polyamines with two or more primary and/or secondary amino groups, which react in situ to form a crosslinked, non-linear network. The network formation is essential to achieve desired shrinkage control and/or durability to dry-cleaning.

It is also known that fluorochemicals, such as SCOTCHGARD® FC-248 (3M), are effective soil release treatments for textile substrates. However, fabrics treated with SCOTCHGARD® FC-248, especially in combination with durable press finishes, become very harsh and unpleasant to wear. Although improvement in "hand" is desirable, according to the SCOTCHGARD® FC-248 Product Bulletin, polysiloxanes are believed to severely affect performance properties of the fluorochemical.

SUMMARY OF THE INVENTION

The present invention discloses non-hydrolyzable, block, $(AB)_nA$ type, copolymers comprising alternating units of polysiloxane and amino-polyalkyleneoxide and provides a method for the preparation of these copolymers. Also provided is the use of these copolymers as softeners, in particular durable, hydrophilic textile softeners, which improve tactile properties of the textile substrates treated with the commercial soil release finishes, without detracting from their properties. Other uses include treating relatively hydrophobic substrates such as woven and non-woven substrates to impart durable softness and hydrophilicity thereto. Other uses include personal care formulations containing these copolymers, and substrates which have been treated with these copolymers.

DETAILED DESCRIPTION OF THE INVENTION

A. Copolymer Structure

The copolymers of the present invention have alternating units of polysiloxane $[X(C_aH_{2a}O)_bR^2[(SiO(R^1)_2]_cSi(R^1)_2R^2(OC_aH_{2a})_bX]$ and polyalkyleneoxides $[YO(C_aH_{2a}O)_dY]$ wherein $R^1$ is a $C_1$ to $C_4$ alkyl, preferably methyl, $R^2$ is a divalent organic moiety, X and Y are divalent organic groups selected from a secondary or tertiary amine and a ring opened epoxide, such that when X is a ring opened epoxide, Y is an amine and vice versa, a is 2 to 4, preferably 2 to 3, each occurrence of b is 0 to 100, d is 0 to 100, (b+d) is 1 to 100, preferably 10 to 50, and c is 1 to 500, preferably 10 to 100. The total number of repeating units is limited only by the ability to handle high viscosity material, since the viscosity increases as does the number of units, but practically there should be at least two of each unit and may be up to 1,000 units. It is preferred that the unit containing the amine should be the terminal units of the copolymer, i.e., the A in $(AB)_nA$.

The ring opened epoxides, represented by either X or Y, may be aliphatic, cycloaliphatic, and may contain aromatic rings. They also contain hydroxy groups and may contain an ether linkage. Preferably the ring opened epoxide is chosen from the following:
—CH$_2$CH(OH)(CH$_2$)$_v$CH(OH)CH$_2$—, —CH[CH$_2$OH](CH$_2$)$_v$CH[CH$_2$OH]—, —CH$_2$CH(OH)(CH$_2$)$_v$CH[CH$_2$OH]—, —(CH$_2$)$_v$—OCH$_2$CH(OH)CH$_2$—; —(CH$_2$)$_v$OCH$_2$CH(CH$_2$[OH])— with v=2 to 6. Alternatively, the ring opened epoxides may be derived from the following epoxycyclohexyl alkylene groups, ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

The amines, represented by either X or Y, are secondary or tertiary amines. More specifically, the amines may be of the type —R$^4$N(R$^3$)(R$^4$)$_g$—, where R$^3$ may be an alkyl group with 1 to 4 carbons or hydrogen, most preferably methyl, and R$^4$ is an alkylene, cycloaliphatic alkylene or an aralkylene group, which may include heteroatoms, though an allylene of less than ten carbons is preferred, and g may be 0 or 1.

R$_2$ is a divalent hydrocarbon group with at least one carbon, which may have hydroxy substitutions thereon and/or include an ether linkage. It is preferred that it contain less than ten carbons. Within a particular $(AB)_nA$ molecule each R$^1$, R$^2$, R$^3$ and R$^4$ may be the same or different.

The polyoxyalkylene blocks represented by $(C_aH_{2a}O)$ or $(OC_aH_{2a})$ may be made up of ethylene oxide (a=2), propylene oxide (a=3) and butylene oxide (a=4) in a random or blocked fashion. The ratio among such oxides is not of particular importance, but may be adjusted as required for the desired solubility parameters of the resulting copolymer.

The molecular weight of the copolymers can be modified by varying the molar ratio of the epoxy component to amino component, by varying the number of oxyalkylene units and the number of siloxy groups within the polysiloxane blocks. Although it is important to generate materials with high molecular weight because properties essential to the application, such as softness and durability, are dependent upon the molecular weight of the polymer, it is also essential to produce, non-crosslinked structures, i.e., only linear molecules.

Another important factor controlling the properties of the copolymers is relative silicone content in the molecule, i.e., the values of c, and (b+d). Higher silicone content copolymers are usually more hydrophobic, therefore less water soluble and impart better softness. A preferred ratio of c to (b+d) is 10:1 to 1:10, and most preferably 2:1.

The copolymers are terminated with hydrogen, when the terminal groups are ring opened epoxides. When the terminal groups are amines as described herein, the copolymers are terminated with primary aor secondary amine groups.

A particularly preferred copolymer may be of the following formula:

HN(R$^3$)(C$_a$H$_{2a}$O)$_b$CH(CH$_3$)CH$_2$N(R$^3$)
[CH$_2$CH(OH)CH$_2$O(CH$_2$)$_3$(SiO(R$^1$)$_2$)$_c$Si(R$^1$)$_2$(CH$_2$)$_3$OCH$_2$—
CH(OH)CH$_2$—N(R$^3$)(C$_a$H$_{2a}$O)$_b$CH$_2$CH(CH$_3$)N(R$^3$)]$_y$H. 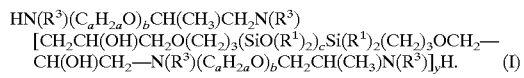

"y" is at least two and may be as high as allowable within the art of manufacturing high viscosity compositions and thus may range from 2 to about 1,000, depending on the values of b and c in formula (I).

B. Method of Manufacture

Preparation of the compounds of the present invention is by reacting two species $Q(C_aH_{2a}O)_bR^2[(SiO(R^1)_2]_cSi(R^1)_2R^2(OC_aH_{2a})_bQ$ and polyalkyleneoxides $[ZO(C_bH_{2b}O)_dZ]$, which are the same as the formulae above except that each Q and Z are either a primary or secondary amine or an epoxide containing group, with the proviso that if Q contains an amine, Z contains an epoxide and vice versa. These species may be manufactured as is known in the art or are commercially available.

In an exemplary process, α,ω-hydrogenpolysiloxanes of the general formula $H(SiO(R^1)_2)_xSi(R^1)_2H$ are reacted with the unsaturated epoxides with a terminal olefinic bond, such as allyl glycidyl ether, in the presence of a hydrosilation catalyst, such as for example hexachloroplatinic acid, at elevated temperature, to produce epoxy endblocked polysiloxanes. Such procedures are known in the art as indicated in U.S. Pat. No. 3,761,444 or British Patent No. 1,213,779. Examples of suitable epoxides with terminal olefinic groups are given below:

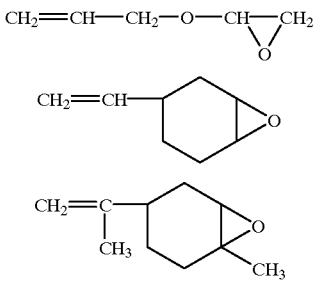

In the second step, the epoxy endblocked polysiloxanes are reacted with polyalkyleneoxides terminated with primary or secondary amino groups. Such aminopolyalkyleneoxides are represented by JEFFAMINE® ED-900 and JEFFAMINE® ED-2001 available from Huntsman Co. and may be of the following structure: $H_2NCH(CH_3)CH_2(OC_aH_{2a})_bOCH_2CH(CH_3)NH_2$ (II).

The reaction is carried out in a suitable solvent, such as alcohol or mixture of alcohol and water at reflux. Typically, epoxy endblocked polysiloxanes are added to the solution of the amine in the reaction solvent.

Similarly, the α,ω-hydrogensiloxane may be hydrosilated with an allyl started epoxy terminated polyoxyalkylene oxide as is known in the art. Said epoxy terminated compositions then may be reacted with diamines (e.g., ethylene diamine, 1,6-diaminohexane, piperazine) to link the polyether siloxane units together. Other methods of manufacturing the present structures will be clear to one of skill in the art.

For practical purposes, the reaction is carried out with an 1 to 30%, preferably 1 to 10%, excess of the amine containing species. Despite the fact that the excess of the amine is used during the preparation of the copolymers and the majority of the endgroups is expected to be amines, it is possible that the epoxy end group on the polysiloxane can undergo side reactions with the solvent, water or alcohol to form the corresponding diol or ether alcohol.

After the reaction, the solution of the copolymer can be neutralized by a direct addition of the Bronstedt acid such as acetic acid, citric acid or tartaric acid, undergo solvent exchange with a non-flammable solvent such as water, propylene glycol, dipropylene glycol and dipropylene glycol methyl ether. A reaction product can be also isolated by distilling off the solvent at atmospheric or reduced pressure; depending on the molecular weight and ethylene oxide content of the copolymer it may be a viscous oil or a wax.

C. Copolymer Uses

The copolymers of the present invention are primarily intended as softeners for substrates, especially fiber, hair and textiles, and particularly in stain release formulations incorporating a fluorochemical. While the copolymers of the present invention can be used neat, for ease of application they are usually applied to the substrates dissolved, dispersed or emulsified to a suitable liquid medium. Preferably, the copolymers of the present invention are applied to a substrate from an aqueous solution, emulsion or suspension. They may also be applied as a solution in a non-aqueous solvent such as isopropanol, or in liquid in which the copolymer is miscible. Most preferably, the copolymer is applied to a substrate as an aqueous dispersion.

Aqueous emulsions of the copolymers are prepared by combining the copolymer with one or more emulsifiers such as nonionic surfactants and diluted with water to the desired concentration. Nonionic surfactants commonly employed in such emulsions can include, for example, TERGITOL® surfactants available from Union Carbide Chemicals and Plastics Co., Inc.

Stable aqueous dispersions of the copolymers can be, for example, prepared by directly blending or mixing a solution of the copolymer in the water miscible solvent, such as isopropanol, propylene glycol, dipropylene glycol and dipropylene glycol methyl ether, with water to obtain desired copolymer level.

Thus prepared dispersions, emulsions or solutions can be applied onto the substrate such as by spraying, dipping or kiss roll application or other application method typically employed in fiber, hair or textile treatment. The substrate which can be treated with the copolymers of the present invention is exemplified by natural fibers such as hair, cotton, silk, flax, cellulose, paper (including tissue paper) and wool; synthetic fibers such as polyester, polyamide, polyacrylonitrile, polyethylene, polypropylene and polyurethane; and inorganic fibers such as glass or carbon fibers. The fabric substrate which can be treated with the copolymers of the present invention is exemplified by the fabric produced from the above-mentioned fibrous materials or blends thereof.

In general the dispersion is applied on skin, hair, fiber or textile such that up to 5%, preferable 0.25 to 2.5% of the copolymer by weight of the dry substrate remains on the substrate. Optionally other additives, commonly used to treat hair or textile substrates can be employed along with the copolymers of the present invention, including but not limited to additional surfactants, curing resins, preservatives, dyes, colorants, formularies, and/or perfluorinated stain/soil release finishes.

Moreover, compositions including the $[AB]_nA$ copolymers of the present invention may be used in personal care formulations, including cleansers, body washes, soaps, lotions, creams, shaving cream, hair sprays, conditioners, shampoos, deodorants, moisturizers, and sunblocks.

The copolymers of the present invention can be formulated into these or other products together with one or more anionic surfactants, one or more amphoteris surfactants, one or more nonionic surfactants, and/or one or more thickeners.

Suitable anionic surfactants include sulfonated and sulfated alkyl, aralkyl and alkaryl anionic compounds; alkyl succinates; alkyl sulfosuccinates; and N-alkanoyl sarcosinates. Preferred are the sodium, magnesium, ammonium, and the mono-, di- and triethanolamine salts of alkaryl sulfonates. The alkyl groups preferably contain 8 to 22 carbon atoms. Sulfate ethers are contemplated, preferably containing 1 to 10 ethylene oxide and/or propylene oxide units. Preferred examples of anionic surfactants include sodium lauryl sulfate, sodium lauryl ether sulfate, ammonium lauryl sulfate, triethanolamine lauryl sulfate, sodium C14–16 olefin sulfonate, ammonium pareth-25 sulfate, sodium myristyl ether sulfate, ammonium lauryl ether sulfate, disodium monooleamido-sulfosuccinate, ammonium lauryl sulfosuccinate, sodium dodecylbenzene sulfonate, triethanolamine dodecylbenzene sulfonate and sodium N-lauroyl sarcosinate.

Examples of amphoteric surfactants with which the copolymers of the present invention can be formulated include cocoamphocarboxyglycinate, cocoamphocarboxypropionate, cocobetaine, N-cocoamidopropyldimethylglycine, and N-lauryl-N'-carboxymethyl-N'-(2-hydroxyethyl)ethylenediamine, as well as the betaine and sultaine compounds disclosed in the CTFA Dictionary as useful in personal care products.

Examples of useful nonionic surfactants with which the copolymers of the present invention can be formulated include fatty acid mono- and dialkanolamides in which the fatty portion preferably contains 10–21 carbon atoms, and amine oxides such as N-alkyl amine oxides.

A typical shampoo formulation contains about 3 to 30 weight percent of an anionic and/or amphoteric surfactant component, 0.1 to 10 weight percent of a nonionic surfactant component, together with 0.1 to 20 weight percent of one or more copolymers of the present 29602 invention, and water, preferably also with an effective amount on the order of 0.1 to 5 weight percent of a thickener; examples of thickeners include sodium alginate, gum arabic, polyoxyethylene, guar gum, hydroxypropyl guar gum, cellulosics such as methyl cellulose, methylhydroxypropyl cellulose, and hydroxypropylcellulose, starch derivatives such as hydroxyethylamylose, locust bean gum, and polysaccharides.

EXAMPLES

Synthetic procedures for the preparation of the copolymers of the invention, as well as their application are described in the following examples, which are provided by way of illustration and not by way of limitation.

Example 1

Preparation of the $(AB)_nA$ Copolymers of the Invention

In a 1L 4-neck flask equipped with stirrer, addition funnel and reflux condenser, α,ω-hydrogensiloxane (charges provided in Table 1 corresponding to a molar excess of the epoxide) of the general formula $HSi(CH_3)_2O[Si(CH_3)_2O]_pSi(CH_3)_2H$ was heated to 80° C. A slow addition of the allyl glycidyl ether started at 80° C. after chloroplatinic acid (5 to 10 ppm as Pt) was added to the pot. The temperature was maintained at 80 to 90° C. until no SiH could be detected. The excess allyl glycidyl ether was removed by vacuum strip at 50 mm Hg and 120° C.; the resulting epoxy endblocked fluid was characterized by its epoxy equivalent weight.

TABLE 1

Charges for the Preparation of the Epoxyendblocked Polysiloxanes

| p | SiH Charge (g) | Allyl Glycidyl Ether Charge (g) | Designation of the Epoxy Fluid | Epoxy Equivalent Weight (g) |
|---|---|---|---|---|
| 20 | 500 | 91.7 | A-20 | 781.3 |
| 50 | 500 | 31.2 | A-50 | 2127 |
| 75 | 500 | 21.0 | A-75 | 3030 |
| 100 | 500 | 15.9 | A-100 | 3703 |
| 150 | 500 | 11.2 | A-150 | 4761 |

In a second step, the aminopolyalkyleneoxide (5% molar excess) [JEFFAMINE® ED-900 is pursuant to Formula II above with a=2.5 and b=15.5 and JEFFAMINE® ED 2001 is pursuant to Formula II above with a=2.5 and b=40.5] detailed charges provided in Table 2 and a sufficient amount 2-propanol to make a 50% solution of the final copolymer, were placed in a 1L four neck flask, equipped with a stirrer, addition funnel, reflux condenser and thermometer. The temperature of the reaction mixture was adjusted to 80° C. and an α,ω-diepoxysiloxane was added from an addition funnel in three portions, allowing 1–2 hrs between additions. The reaction was complete when the epoxy functionality, determined by titration, was consumed.

TABLE 2

Charges for the Preparation of the $(AB)_nA$ Copolymers

| Starting Epoxy Fluid | Charge of the Epoxy Silicone (g) | JEFFAMINE® ED-900 (g) | JEFFAMINE® ED-2001 (g) | Designation of the Copolymer |
|---|---|---|---|---|
| A-20 | 50 | 30.5 | | AB-20-18 |
| A-20 | 50 | | 69.8 | AB-20-43 |
| A-50 | 100 | 30.0 | | AB-50-18 |
| A-50 | 100 | | 61.0 | AB-50-43 |
| A-75 | 200 | | 75.5 | AB-75-43 |
| A-100 | 300 | 40.1 | | AB-100-18 |

TABLE 2-continued

Charges for the Preparation of the (AB)$_n$A Copolymers

| Starting Epoxy Fluid | Charge of the Epoxy Silicone (g) | JEFFAMINE ® ED-900 (g) | JEFFAMINE ® ED-2001 (g) | Designation of the Copolymer |
|---|---|---|---|---|
| A-100 | 300 | | 94.5 | AB-100-43 |
| A-150 | 200 | | 49.0 | AB-150-43 |

Example 2

Testing Softening Properties of (AB)$_n$A Copolymers.

In this example the test fabric and test procedures used were as follows:

Bleached Cotton Interlock Knit, Style 460 (Test Fabrics Inc., Middlesex N.J.)

Test Procedures

Conditioning Textiles for Testing, ASTM Method D-1776-79

Absorbency of Bleached Textiles, AATCC Method 79-1992

Softness evaluation was done by the hand panel and the tested fabrics were ranked from the softest to the hardest (1 being the softest).

Selected copolymers of the present invention (as solutions in isopropanol), MAGNASOFT® PLUS (control, commercial premium amino softener from OSi Specialties, Inc. of Danbury, Conn.) and MAGNASOFT® HSSD (control, hydrophilic softener with pendant polyalkyleneoxide and amino groups from OSi Specialties) were applied onto 100% cotton knit from the pad bath. A durable press resin (methylated dimethyloldihydroxyethylene urea, which is commercially available) and curing catalyst (magnesium chloride) were used with all treatments to simulate typical textile finishing procedure. The softener concentration in the finishing composition was such that the effective add-on level on the fabric was 1%; curing conditions were 171° C. for 1.5 minutes. Softening and absorbency data are summarized in Table 3.

TABLE 3

Softness Ranking and Wettability

| Softener | Softness Ranking | Wetting time (sec) |
|---|---|---|
| AB-150-43 | 3 | 3.5 |
| AB-100-43 | 2 | 4.0 |
| AB-75-43 | 4 | 7.0 |
| MAGNASOFT ® Plus | 1 | 66.0 |
| MAGNASOFT ® HSSD | 5 | 1.0 |

[1]Higher reflectance values correspond to whiter fabrics
[2]Lower ranks correspond to softer fabrics Table 3 demonstrates that (AB)$_n$A copolymers, in the presence of the durable press resin provided softening properties superior to MAGNASOFT® HSSD silicone and wetting properties superior to MAGNASOFT® PLUS silicone.

Example 3

Testing Hair Conditioning Properties

In a side-by-side comparison test, one half of an amount of human hair was washed with a control shampoo and the other half was washed using a conditioning shampoo containing the present disclosed product. Combability, appearance and fly-away data are summarized in Table 4.

SHAMPOO PREPARATION

| | Control Shampoo (Wt %) | Conditioning Shampoo (Wt %) |
|---|---|---|
| Ammonium Lauryl Sulfate, 28% | 35.0 | 35.0 |
| Lauramide DEA | 3.0 | 3.0 |
| PEG-120 Methyl Glucose Dioleate "Glucamate" DOE-120[a] | 2.0 | 2.0 |
| AB-100-43 (25% in dipropylene glycol) | | 12.0 |
| Citric Acid, anhydrous | 0.4 | 0.4 |
| Cocamidopropyl Betaine, 35% | 10.0 | 10.0 |
| Dimethicone Copolyol, SILWET ® surfactant L-7657[b] | 2.5 | 2.5 |
| Deionized Water | qs | qs |
| Preservative | qs | qs |

[a]: Amerchol
[b]: OSi Specialties, Inc.

Procedure: Water was mixed with ammonium lauryl sulfate. The solution was heated to 45° C. and the remaining ingredients were added in the order listed, waiting for each ingredient to dissolve before adding the next. Preservative was added after cooling the formulation to room temperature.

TABLE 4

Properties of Hair treated with Copolymer AB-100-43

| TREATMENT | COMBABILITY WET (INCHES) | COMBABILITY DRY (INCHES) | FLY-AWAY (INCHES) | APPEARANCE |
|---|---|---|---|---|
| Control | 2.7 | 5.0 | 10.0 | smooth, dull |
| Conditioning Shampoo | 4.8 | 9.0 | 5.0 | silky soft, glossy |

Hair washed with the conditioning shampoo had improved wet and dry combability, provided better gloss and reduced electrostatic charge.

Example 4

Testing $(AB)_nA$ Copolymers in Combination with Stain Release Agent

In this example the stain release agent, test fabric and test procedures used were as follows:

Fluorocarbon Stain Release Agent—SCOTCHGARD® FC-248 fluorocarbon, 30% aqueous dispersion (3M)

Fabrics Identification (Test Fabrics Inc., Middlesex N.J.)—Bleached Cotton Interlock Knit, Style 460; 65/35 Polyester Cotton Bleached Broadcloth, Style 7409

Test Procedures

Soil Release: Oily Stain Release AATCC Method 130-1990

Conditioning Textiles for Testing, ASTM Method D-1776-79

Reflectance, Blue and Whiteness of the Bleached Fabric, AATCC Method 110-1979

Softness evaluation was done by the hand panel and the tested fabrics were ranked from the softest to the harshest (1 being the softest).

Selected inventive copolymers, MAGNASOFT® PLUS (control, commercial premium amino softener) and MAGNASOFT® HSSD (control, hydrophilic softener with pendant polyalkyleneoxide and amino groups) silicones were padded onto 100% cotton knit and 100% cotton woven, in combination with SCOTCHGARD® FC-248. A durable press resin (methylated dimethyloldihydroxyethyleneurea, which is commercially available) and curing catalyst (magnesium chloride) were used with all treatments to simulate typical textile finishing procedure. The softener and stain release agent concentrations in the finishing composition were such that the effective actives add-on levels on the fabric were 0.5% (BOWF); curing conditions were 171° C. for 1.5 minutes.

Whiteness of the treated fabrics was determined using a spectrocolorimeter from Hunter Lab. Softness and reflectance data are given in Table 5.

TABLE 5

Reflectance and Softness Data for Fabrics Treated with $(AB)_nA$ Copolymers and Control Softeners

| | 100% COTTON KNIT | |
|---|---|---|
| FINISH | Reflectance[1] | Softness Rank[2] |
| AB-20-18 | 63.8 | 5 |
| AB-20-43 | 73.2 | 9 |
| AB-50-18 | 65.9 | 8 |
| AB-75-43 | 68.6 | 1 |
| AB-100-18 | 71.0 | 6 |
| AB-100-43 | 71.1 | 2 |
| AB-150-43 | 72.0 | 3 |
| MAGNASOFT ® PLUS (control) | 69.8 | 4 |
| MAGNASOFT ® HSSD (control) | 75.7 | 6 |
| No Silicone | 72.9 | 10 |

[1]Higher values correspond to whiter fabrics
[2]Lower ranks correspond to softer fabrics Based on the data contained in Table 5, all copolymers of the present invention improved the "hand" of the fabrics treated with the perfluoro stain release finish without discoloring the fabrics.

Treated fabrics were subsequently stained with dirty motor oil, mineral oil and corn oil, according to ASTM 130-1990, washed once and evaluated. Stain release ratings for dirty motor oil stain are summarized in Table 6.

TABLE 6

Stain Release Ratings of Fabrics Treated with Scotchgard in Combination with $(AB)_nA$ Copolymers and Control Softeners

| FINISH | STAIN RELEASE RATING[1] 100% Cotton Knit | STAIN RELEASE RATING 65/35 Polyester Cotton |
|---|---|---|
| AB-20-18 | 3.0 | 3.75 |
| AB-20-43 | 3.5 | 3.5 |
| AB-50-18 | 3.5 | 3.75 |
| AB-75-43 | 3.0 | 3.5 |
| AB-100-18 | 3.5 | 4.0 |
| AB-100-43 | 2.5 | 3.75 |
| AB-150-43 | 3.0 | 3.5 |
| MAGNASOFT ® PLUS | 1.5 | 1.5 |
| MAGNASOFT ® HSSD | 2.5 | 3.5 |
| No Silicone | 3.75 | 3.75 |

[1]Soil Release rating: 1 = most visible; 5 = invisible

As demonstrated in Table 6, copolymers of the present inventions, are useful as softeners for the stain release finishes, since they, unlike traditional hydrophobic softeners, have only minimal effect on the performance of the perfluoro chemical.

Example 5

Testing $(AB)_nA$ Copolymers for Softening and Wettability of Facial Tissue

Aqueous solutions or dispersions of the copolymers of the present invention identified in Table 7 were spray applied to both sides of conventional 3-ply facial tissue such that 2.0 weight percent silicone solids were present on the tissue after air drying. Blind samples (including controls) were evaluated by 5 panelists and rated for softness, and the average of the ratings for each sample were recorded and reported in Table 7. The rating scale ranged from 1 (softest) to 14 (harshest). Also, wettability was tested in accordance with AATCC test protocol 79-1995.

TABLE 7

Evaluation of $(AB)_nA$ Copolymers on 3-Ply Facial Tissue

| PRODUCT TESTED | WETTABILITY, sec. | SOFTNESS RATING |
|---|---|---|
| AB-20-43 | 4 | 4.4 |
| AB-100-43 | >180 | 5.6 |
| AB-20-18 | 4 | 3.4 |
| AB-50-43 | 15 | 8.6 |
| AB-50-18 | 14 | 3.8 |
| Commercial Silicone Softener | 2 | 12.3 |
| Water Control | 1 | 14 |

All materials in accordance with the present invention which were tested showed excellent softening properties, superior to an existing commercial product, and most showed good wetting characteristics.

Example 6

Hydrophilic Durability of $(AB)_nA$ Copolymers on Nonwoven Polypropylene

Another use for the copolymers of the present invention is in surface application to normally hydrophobic substrates such as nonwoven polypropylene, in order to increase the wettability of the substrate. A product that would be used for this purpose should be able to resist being washed off of the substrate when aqueous fluids are applied to the substrate.

One established technique for assessing the ability of surface treatments to resist being washed off is to apply the product, and subject it to repeated treatment ("insults") with an aqueous solution, and to measure the amount of the product remaining on the substrate after each insult. This technique was used in this Example.

Aqueous solutions or dispersions of $(AB)_nA$ copolymers of the present invention identified in Table 8 were prepared and spray applied to one side of 100% polypropylene (0.65 oz/yd$^2$) nonwoven fabric such that 0.5% silicone solids was present on the nonwoven after air drying. The samples, and controls, were assessed for hydrophilic durability to repeated insults (using 0.9% NaCl aqeous solution) using EDANA Test Method 150.3-96 (Liquid Strike Through Time). The results are reported in Table 8. Keeping in mind that the objective is to continue to impart wettability even after repeated insults, a low number in the table is preferred as representing a shorter time needed to wet the substrate and, accordingly, a higher proportion of the product remaining on the substrate.

TABLE 8

Evaluation of $(AB)_nA$ Copolymers on 100% Polypropylene Nonwoven

| | Time in Seconds Required to Wet the Substrate After Each Insult | | | | |
|---|---|---|---|---|---|
| No. of Insults = | 1 | 2 | 3 | 4 | 5 |
| Product Tested: | | | | | |
| AB-20-18 | 14.6 | 9.9 | 11.1 | 12.1 | 11.3 |
| Silicone Copolymer w/Pendant Polyalkoxy Chains (control) | 2.8 | 4.0 | 43.1 | 67.7 | 93.2 |
| AB-20-43 | 42 | 32 | 30.4 | 15.0 | 23.1 |
| Untreated | >180 | >180 | >180 | >180 | >180 |

The data in Table 8 show that the copolymers of the present invention are more hydrophilically durable after repeated insults than conventional silicone copolymers with pendant polyalkyleneoxide side chains.

What is claimed is:

1. A copolymer comprising alternating units of formula $(X(C_aH_{2a}O)_bR_2(SiO(R^1)_2)_cSi(R^1)_2R^2(OC_aH_{2a})_bX(1)$ and formula $(YO(C_aH_{2a}O)_dY)(2)$ wherein each $R^1$ is independently a $C_1$ to $C_4$ alkyl group, $R^2$ is a divalent organic moiety, X is a secondary or tertiary amine, Y is a ring opened epoxide, a is 2 to 4, each occurrence of b is 0 to 100, d is 0 to 100, (b+d) is 1 to 100, and c is 1to 500.

2. A copolymer according to claim 1 wherein said secondary and tertiary amines correspond to the structure —$R^4N(R^3)(R^4)_g$—, wherein $R^3$ is an alkyl group with 1 to 4 carbon atoms or hydrogen, $R^4$ is an alkylene, cycloaliphatic alkylene or an aralkylene group which may include heteroatoms, and g is 0 or 1.

3. A copolymer according to claim 1 which is of the formula $(AB)_nA$ wherein each A is a unit of formula (1) which is terminated with a secondary or tertiary amine, each B is a unit of formula (2) which is terminated with ring opened epoxide, and n is 2 to 1,000.

4. A copolymer according to claim 1 wherein a is 2 or 3.

5. A copolymer according to claim 1 wherein (b+d) is 10 to 50.

6. A copolymer according to claim 1 wherein each $R^1$ is methyl.

7. A copolymer according to claim 1 wherein the ratio of c to (b+d) is 10:1 to 1:10.

8. A copolymer according to claim 1 wherein the ring opened epoxide is selected from the group consisting of $CH_2CH(OH)(CH_2)_vCH(OH)CH_2$—, —$CH(CH_2OH)CH_2)_vCH(CH_2OH)$—, —$CH_2CH(OH)(CH_2)_vCH(CH_2OH)$—, —$(CH_2)_vOCH_2CH(OH)CH_2$—, and $(CH_2)_vOCH_2CH(CH_2(OH))$— in each of which v is 2 to 6.

9. A substrate comprising on at least one surface thereof a copolymer according to claim 1.

10. A substrate according to claim 9 wherein said substrate is selected from the group consisting of natural and synthetic fibers and nonwoven materials.

11. A method of imparting durable hydrophilicity to a substrate comprising applying to said substrate a copolymer according to claim 1.

12. A method according to claim 11 wherein said substrate is selected from the group consisting of natural and synthetic fibers and nonwoven materials.

13. A method of imparting durable softness to a substrate comprising applying to said substrate a copolymer according to claim 1.

14. A method according to claim 13 wherein said substrate is selected from the group consisting of natural and synthetic fibers and nonwoven materials.

15. A personal care formulation comprising a copolymer according to claim 1, a surfactant component, and water.

16. A personal care formulation according to claim 15 further comprising a thickener.

17. A personal care formulation which is a shampoo comprising a copolymer according to claim 1, a surfactant component selected from the group consisting of anionic surfactants, amphoteric surfactants, and mixtures thereof, a nonionic surfactant, a thickener component, and water.

18. A copolymer according to claim 1 wherein the ring opened epoxide is derived from the epoxide selected from the group consisting of ω-(3,4-epoxycyclohexyl)alkylene, β-(3,4-epoxycyclohexyl)ethylene, β-(3,4-epoxycyclohexyl)-β-methylethylene, and β-(3,4-epoxy-4-methylcyclohexyl)-β-methylethylene.

* * * * *